United States Patent
Knappe et al.

(10) Patent No.: US 10,357,443 B2
(45) Date of Patent: Jul. 23, 2019

(54) ACTIVE-SUBSTANCE MIXTURES FOR STYLING AGENTS

(71) Applicant: Henkel AG & Co. KGaA, Duesseldorf (DE)

(72) Inventors: Thorsten Knappe, Schenefeld (DE); Ulrike Heinsohn, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/363,797

(22) Filed: Nov. 29, 2016

(65) Prior Publication Data

US 2018/0147132 A1 May 31, 2018

(30) Foreign Application Priority Data

Dec. 16, 2015 (DE) .................. 10 2015 225 420

(51) Int. Cl.
| | | |
|---|---|---|
| *A61K 8/73* | (2006.01) | |
| *A61K 8/04* | (2006.01) | |
| *A61K 8/67* | (2006.01) | |
| *A61K 8/49* | (2006.01) | |
| *A61K 8/36* | (2006.01) | |
| *A61K 8/58* | (2006.01) | |
| *A61K 8/81* | (2006.01) | |
| *A61K 8/25* | (2006.01) | |
| *A61K 8/365* | (2006.01) | |
| *A61Q 5/06* | (2006.01) | |

(52) U.S. Cl.
CPC .............. *A61K 8/736* (2013.01); *A61K 8/046* (2013.01); *A61K 8/25* (2013.01); *A61K 8/36* (2013.01); *A61K 8/365* (2013.01); *A61K 8/4913* (2013.01); *A61K 8/585* (2013.01); *A61K 8/675* (2013.01); *A61K 8/8176* (2013.01); *A61K 8/8182* (2013.01); *A61Q 5/06* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 2004/0228809 A1* | 11/2004 | Birkel | ................... | A61K 8/046 |
| | | | | 424/47 |
| 2006/0246027 A1* | 11/2006 | Tanner | ................ | A61K 8/0212 |
| | | | | 424/70.12 |
| 2015/0004116 A1 | 1/2015 | Tan et al. | | |

FOREIGN PATENT DOCUMENTS

| | | |
|---|---|---|
| WO | 2009027943 A2 | 3/2009 |
| WO | 2013165424 A1 | 11/2013 |
| WO | 2014210466 A1 | 12/2014 |

OTHER PUBLICATIONS

Intellectual Property Office, Combined Search and Examination Report under Sections 17 and 18(3) for United Kingdom Application No. GB1621330.8 dated Oct. 4, 2017.

* cited by examiner

*Primary Examiner* — Kevin S Orwig
*Assistant Examiner* — Barbara S Frazier
(74) *Attorney, Agent, or Firm* — Lorenz & Kopf, LLP

(57) ABSTRACT

Cosmetic agents and methods for temporarily shaping keratin-containing fibers using the cosmetic agents are provided herein. In one embodiment, the cosmetic agent includes a cosmetic carrier. The cosmetic agent further includes at least one chitosan or derivative thereof. The cosmetic agent further includes at least one hydrophobic pyrogenic silicic acid. The cosmetic agent also includes at least one non-ionic, anionic, or amphoteric film-forming polymer. In another embodiment, the method includes the step of using the cosmetic agent for temporarily shaping keratin-containing fibers.

13 Claims, No Drawings

ACTIVE-SUBSTANCE MIXTURES FOR STYLING AGENTS

CROSS-REFERENCE TO RELATED APPLICATION

This application claims priority to German Patent Application No. 10 2015 225 420.8, filed Dec. 16, 2015, which is incorporated herein by reference in its entirety.

TECHNICAL FIELD

The present disclosure relates to cosmetic agents for temporarily shaping keratin-containing fibers that contain a combination of at least one chitosan compound, one hydrophobic silicic acid, and one film-forming polymer in a cosmetic carrier.

BACKGROUND

The disclosure also relates to the use of the cosmetic agents to increase the volume and the body of hair and to improve the curl retention, particularly the high-humidity curl retention.

Agents for temporary shaping are known per se. They usually contain synthetic polymers as a shaping component. Preparations that contain a dissolved or dispersed polymer can be applied to the hair by means of propellant gases or a pumping mechanism. However, hair gels and hair waxes, in particular, are generally not applied directly to the hair but rather are distributed in the hair by means of a comb or one's hands.

The most important property of an agent for temporarily shaping keratin-containing fibers, hereinafter also called a styling agent, is that of giving the treated fibers the strongest possible hold in the produced shape. If the keratin-containing fibers are human hair, this hold is also called strong hairstyle hold or high degree of hold of the styling agent.

Cosmetic styling agents generally contain individual polymers that are specifically tailored to achieving a very particular effect. If various effects should be achieved, several polymers must be added. However, if too many different polymers are used, this can result in several disadvantages. Problems can arise with respect to the formulation, for example because the polymers react among each other or with other constituents of the agent and precipitations or decompositions occur. Certain polymers also tend to deposit on the skin and particularly on the hair so durably that said polymers are no longer completely removed in a typical washing and undesired accumulation of the polymer and therefore in the end a strain on the skin or hair occur.

Therefore, there is always a need for polymers or suitable combinations of a few polymers that have as many of the desired properties as possible.

For example, it is necessary in the case of the styling agents that the polymers used give the treated hair the strongest possible hold. However, styling agents must meet a whole series of other requirements in addition to a high degree of hold. These requirements can be roughly divided into properties on the hair, properties of the particular formulation, e.g., properties of the foam, the gel, or the sprayed aerosol, and properties that affect the handling of the styling agent, wherein the properties on the hair are especially important. In particular, moisture resistance, low tackiness, and a balanced conditioning effect should be mentioned. Furthermore, a styling agent should be universally usable for all hair types, to the extent possible.

The hairstyle hold in general and, for wavy hair, the curl retention in particular are special requirements for styling agents. The curl retention is a measure of the degree of hold of curls. Curl retention is usually worse if the treated hair is in a humid environment, because the tendency of hair to absorb moisture, i.e., water, causes the hair strands to hang limp.

BRIEF SUMMARY

Cosmetic agents and methods for temporarily shaping keratin-containing fibers using the cosmetic agents are provided herein. In one embodiment, the cosmetic agent includes a cosmetic carrier. The cosmetic agent further includes at least one chitosan or derivative thereof. The cosmetic agent further includes at least one hydrophobic pyrogenic silicic acid. The cosmetic agent also includes at least one non-ionic, anionic, or amphoteric film-forming polymer.

In another embodiment, the method includes the step of using the cosmetic agent for temporarily shaping keratin-containing fibers.

DETAILED DESCRIPTION

The following detailed description is merely exemplary in nature and is not intended to limit the invention or the application and uses of the invention. Furthermore, there is not intention to be bound by any theory presented in the preceding background or the following detained description.

It is contemplated herein to address the problem of providing agents for temporarily shaping keratin-containing fibers that provide considerably improved curl retention, particularly considerably improved high-humidity curl retention, i.e., a better degree of hold of curls even in a humid environment, preferably together with additional improvement of the hairstyle hold and of the hair feel (soft texture and elasticity).

It is also contemplated herein to address the problem of increasing and/or maintaining hair fullness, particularly in a humid environment.

These problems were solved by means of a specific active-substance combination, comprising a chitosan, a silicic acid, and a film-forming polymer.

Therefore, a first subject matter of the disclosure is a cosmetic agent for temporarily shaping keratin-containing fibers, particularly human hair, that contains a combination of the active substances a)-c) in a cosmetic carrier:

a) at least one chitosan or derivative thereof,
b) at least one hydrophobic pyrogenic silicic acid, and
c) at least one non-ionic, anionic, or amphoteric film-forming polymer.

As contemplated herein, the term "keratin-containing fibers" should be understood to mean pelts, wool, feathers, and, in particular, human hair.

As contemplated herein, the term "polymers" is understood to mean compounds that are composed of a multitude of molecules in which one or more types of atoms or atom groupings (referred to as constitutive units, basic building blocks, or repeating units) are strung together repeatedly and which have a molecular weight of at least 10000 g/mol. The polymers are obtained by polyreaction, wherein the polyreaction can occur artificially (i.e., synthetically) or naturally.

The agents as contemplated herein contain the active substances thereof in a cosmetic carrier, preferably in a water-containing cosmetic carrier, an alcoholic cosmetic carrier, or an aqueous-alcoholic cosmetic carrier. For the purpose of the temporary shaping of hair, such carriers are, for example, lotions, water-in-oil emulsions, oil-in-water emulsions, creams, gels, foams, pomades, waxes, or other preparations that are suitable for use on the hair.

As contemplated herein, it is preferred that the carrier is a water-containing cosmetic carrier or an aqueous-alcoholic cosmetic carrier. As contemplated herein, it is additionally preferred that the cosmetic carrier of the agent as contemplated herein contains water in such a way that the agent contains at least 50 wt % of water with respect to the weight of the entire agent.

In the sense of the present disclosure, the term "aqueous-alcoholic carriers" should be understood to mean aqueous compositions that contain about 3 to about 70 wt % of a $C_1$-$C_4$ alcohol, particularly ethanol or isopropanol. The agents as contemplated herein can additionally contain other organic solvents, such as methoxybutanol, benzyl alcohol, ethyl diglycol, 1,2-propylene glycol, or 1,3-propylene glycol. All water-soluble organic solvents are preferred.

A preferred embodiment of the disclosure is characterized in that the cosmetic agents contain about 50 to about 95 wt %, especially preferably about 60 to about 92.5 wt %, and particularly about 65 to about 90 wt % of water or a water-alcohol mixture with respect to the total weight of the cosmetic agents.

Chitosans a) are biopolymers and belong to the group of the hydrocolloids. Chemically, chitosans are partially deacetylated chitins of different molecular weight.

In order to produce chitosans, one proceeds from chitin, preferably the shell remains of crustaceans, which are available in large amounts as inexpensive raw materials. The chitin is usually first deprotonated by adding bases, demineralized by adding mineral acids, and finally deacetylated by adding strong bases, wherein the molecular weights can be distributed over a broad range. Types that have an average molecular weight (weight average) of about 800,000 to about 1,200,000 daltons, a viscosity according to Brookfield (1 wt % in glycolic acid) below 5000 mPas, a degree of deacetylation in the range of about 80 to about 88%, and an ash content of less than 0.3 wt % are preferably used.

In addition to the chitosans as typical biopolymers, cationically derivatized chitosans (such as quaternization products) or alkoxylated chitosans as derivatives of chitosan are also possible as contemplated herein.

Agents preferred as contemplated herein are characterized in that said agents contain at least one neutralization product of chitosan with at least one acid as a chitosan a).

Especially preferred agents contain a neutralization product of chitosan with at least one inorganic acid, preferably hydrochloric acid, or with at least one organic carboxylic acid, such as formic acid, acetic acid, citric acid, lactic acid, pyrrolidone carboxylic acid, tartaric acid, glycolic acid, nicotinic acid, hydroxyisobutyric acid, hydroxyisovaleric acid, or mixtures of these acids.

As contemplated herein, it is particularly preferred that the inorganic acid is selected from hydrochloric acid and the organic carboxylic acid is selected from lactic acid, formic acid, pyrrolidone carboxylic acid, nicotinic acid, hydroxyisobutyric acid, hydroxyisovaleric acid, or mixtures of these acids. Said neutralization product can be produced in an aqueous medium by adding chitosan and the corresponding acid, for example.

Suitable chitosans are freely commercially available, for example, under the trade names Hydagen® CMF (1 wt % of active ingredient in an aqueous solution having 0.4 wt % of glycolic acid, molecular weight 500000 to 5000000 g/mol; Cognis), Hydamer® HCMF (chitosan (80% deacetylated), molecular weight 50000 to 1000000 g/mol, Chitinor, formerly Cognis), Kytamer® PC (approximately 80 wt % of active ingredient chitosan pyrrolidone carboxylate (INCI name: Chitosan PCA), Amerchol), Chitolam® NB/101, and Chitosan 90/100/A1® (chitosan (approximately 90% deacetylated); BioLog Heppe).

The at least one chitosan or derivative thereof a) is contained in the agents as contemplated herein preferably in a total amount of about 0.05 wt % to about 1.50 wt %, more preferably about 0.10 wt % to about 1.40 wt %, especially preferably about 0.15 wt % to about 1.25 wt %, and particularly about 0.20 wt % to about 1.00 wt %, wherein the amount specifications relate to the total weight of the cosmetic agent.

The cosmetic agents as contemplated herein contain at least one hydrophobic pyrogenic silicic acid b) as a second essential constituent.

Hydrophobic pyrogenic silicic acids suitable as contemplated herein are preferably modified at the surface of the silicic acid particles with hydrophobic groups, preferably with alkyl groups. Hydrophobic pyrogenic silicic acids suitable as contemplated herein especially preferably contain hydrophobic groups such as $(CH_3)_3Si—O—$, $(—Si(CH_3)_2O—)_n$, $(H_3C)2Si(O)_2—$, and $C_7H_{18}Si(O)_3—$ at the surface.

Alkyl-modified, hydrophobic pyrogenic silicic acids are commercially available, for example from Evonik Degussa under the trade name Aerosil® R. Especially preferred are the commercial products Aerosil® R202, Aerosil® R805, Aerosil® R812, Aerosil® R972, Aerosil® R974, and Aerosil® R976, and additionally products of the Cab-O-Sil® TS series from Cabot, particularly Cab-O-Sil TS-530.

The use of the alkyl-modified, hydrophobic pyrogenic silicic acids known under the INCI name Silica Dimethyl Silylate are particularly preferably used in the agents as contemplated herein. They are available, for example, under the trade names Aerosil® R972 and Aerosil® R974.

The at least one hydrophobic pyrogenic silicic acid b) is contained in the agents as contemplated herein preferably in a total amount of about 0.05 wt % to about 1.50 wt %, more preferably about 0.10 wt % to about 1.40 wt %, especially preferably about 0.15 wt % to about 1.25 wt %, and particularly about 0.20 wt % to about 1.00 wt %, wherein the amount specifications relate to the total weight of the cosmetic agent.

As a third essential constituent, the cosmetic agents as contemplated herein contain at least one non-ionic, anionic, or amphoteric film-forming polymer c), which is not a chitosan or a chitosan derivative.

Polymers that leave behind a continuous film on the skin, the hair, or the nails when drying occurs should be understood by film-forming polymers c). Such film formers can be used in a wide range of cosmetic products, such as face masks, make-up, hair setting lotions, hair sprays, hair gels, hair waxes, hair packs, shampoos, or nail polishes. In particular, polymers that have sufficient solubility in water, alcohol, or water-alcohol mixtures are preferred. In this way, corresponding solutions that can be used or further processed in a simple manner can be produced.

Furthermore, polymers that can deposit a transparent polymer film on the hair when used in a about 0.01 to about 20 wt % aqueous, alcoholic, or aqueous-alcoholic solution are understood by film-forming polymers c) suitable as contemplated herein.

Especially preferred is the use of film-forming polymers c) that also have hair-setting properties at the same time and that can contribute to the hairstyle hold and/or to the build-up of the hair volume and of the hair fullness of the entire hairstyle.

In an especially preferred embodiment, cosmetic agents as contemplated herein contain at least one non-ionic film-forming and setting polymer c).

In this embodiment, cosmetic agents as contemplated herein that contain the at least one non-ionic film-forming polymer c) in a total amount of about 0.10 to about 7.00 wt %, more preferably about 0.20 to about 5.00 wt %, especially preferably about 0.25 wt % to about 4.00 wt %, and particularly about 0.30 to about 3.00 wt % are preferred, wherein the amount specifications relate to the total weight of the cosmetic agent.

The at least one non-ionic film-forming and setting polymer c) can be contained in the cosmetic agents as contemplated herein as a sole polymer or in combination with another non-ionic polymer or in combination with an anionic, amphoteric, or cationic film-forming setting polymer.

As contemplated herein, a polymer which, in a protic solvent and under standard conditions, bears almost no structural units having permanently cationic or anionic groups that must be compensated by counter ions in order to maintain electroneutrality is understood by suitable non-ionic polymers c). Quaternized ammonium groups, for example, fall under cationic groups, but protonated amines do not. Carboxyl and sulfonic acid groups, for example, fall under anionic groups.

Non-ionic film-forming and setting polymers c) especially preferred as contemplated herein can be selected from:

homopolymers and non-ionic copolymers of N-vinylpyrrolidone, such as the commercial products Luviskol® K 90 and Luviskol® K 85 from the company BASF SE, non-ionic copolymers of isobutene, polyvinyl alcohols, which are sold, for example, by DuPont under the trade name Elvanol® and by the company Air Products under the trade name Vinol® 523/540, polyvinyl acetate, which is sold, for example, by the company Air Products as an emulsion under the trade name Vinac®, copolymers of N-vinylpyrrolidone and vinyl acetate, such as the commercial products Luviskol® VA 64 and Luviskol® VA 73 from the company BASF, copolymers of N-vinylpyrrolidone and vinyl esters of carboxylic acids having 2 to 18 carbon atoms, particularly of N-vinylpyrrolidone and vinyl acetate, copolymers of N-vinylpyrrolidone and N-vinylimidazole and methacrylamide, copolymers of N-vinylpyrrolidone and N-vinylimidazole and acrylamide, copolymers of N-vinylpyrrolidone with N,N-di($C_1$ to $C_4$)-alkylamino-($C_2$ to $C_4$)-alkylacrylamide, Other preferred non-ionic film-forming and setting polymers c) are characterized in that said non-ionic film-forming and setting polymers c) contain, as a non-ionic setting polymer, at least one copolymer containing at least one further structural unit of formula (M-I), at least one further structural unit of formula (M-VI), and at least one further structural unit of formula (M-VII),

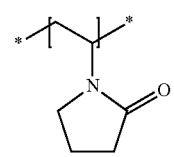

(M-I)

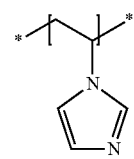

(M-VI)

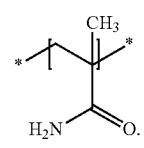

(M-VII)

It is especially preferred if these copolymers contain, in addition to polymer units that result from the incorporation of the mentioned structural units according to formulas (M-IV-a), (M-I), (M-VI), and (M-VII) into the copolymer, at most 5 wt %, preferably at most 1 wt %, of polymer units that trace back to the incorporation of other monomers. Preferably, the copolymers are constructed exclusively of structural units of formulas (M-IV-a), (M-I), (M-VI), and (M-VII) and can be described by general formula (Poly4),

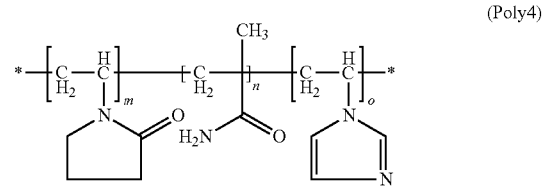

(Poly4)

wherein the indices m, n, o, and p vary in accordance with the molar mass of the polymer and should not mean that the copolymers are block copolymers. Rather, structural units of formulas (M-I), (M-VI), and (M-VII) can be statistically distributed in the molecule.

An especially preferred polymer is selected from the polymers having the INCI name VP/Methacrylamide/Vinyl Imidazole Copolymer, which are available, for example, from BASF SE under the trade name Luviset Clear.

It has been found that an optimal balance between moisture resistance, hold, body, and fullness of the hair can be achieved if the agents as contemplated herein contain a non-ionic film-forming polymer c), preferably at least one homopolymer or copolymer of vinylpyrrolidone and particularly preferably a homopolymer of vinylpyrrolidone, as a polymer c).

Another preferred embodiment of the disclosure is characterized in that the cosmetic agents as contemplated herein contain a vinylpyrrolidone homopolymer (PVP) as at least one non-ionic film-forming polymer c).

Another preferred embodiment of the disclosure is characterized in that the cosmetic agents as contemplated herein contain a vinyl acetate/vinylpyrrolidone copolymer as a non-ionic film-forming polymer c).

Another preferred embodiment of the disclosure is characterized in that the cosmetic agents as contemplated herein contain a mixture of at least one vinylpyrrolidone homopolymer (PVP) and at least one vinyl acetate/vinylpyrrolidone copolymer as a non-ionic film-forming polymer c).

The cosmetic agents as contemplated herein can also contain at least one setting amphoteric polymer as a film-forming polymer c), preferably in combination with at least one of the previously mentioned non-ionic film-forming polymers. The term "amphoteric polymers" comprises polymers that contain both free amino groups and free —COOH or $SO_3H$ groups in the molecule and are capable of forming inner salts, zwitterionic polymers that contain quaternary ammonium groups and —COO⁻ or —$SO_3^-$ groups in the molecule, and polymers that contain —COOH or $SO_3H$ groups and quaternary ammonium groups.

An example of an amphoteric polymer c) that can be used as contemplated herein is the acrylic resin available under the name Amphomer®, which is a copolymer of tert-butylaminoethyl methacrylate, N-(1,1,3,3-tetramethylbutyl) acrylamide, and two or more monomers from the group of acrylic acid, methacrylic acid, and ($C_1$ to $C_4$)-alkyl esters thereof.

The latter have at least one negatively charged group in the molecule in addition to the cationogenic group or positively charged group and are also called zwitteronic polymers.

The setting amphoteric polymers are contained in the cosmetic agents as contemplated herein preferably in amounts of about 0.1 wt % to about 20 wt %, especially preferably about 0.05 wt % to about 10 wt %, with respect to the weight of said preparation. Amounts of about 0.1 to about 5 wt % are exceedingly preferred.

Furthermore, film-forming anionic polymers can be used as film-forming polymers c), preferably in combination with at least one of the previously mentioned non-ionic film-forming polymers.

Anionic polymers are anionic polymers that have carboxylate groups and/or sulfonate groups. Examples of anionic monomers of which such polymers can consist are acrylic acid, methacrylic acid, crotonic acid, maleic anhydride, and 2-acrylamido-2-methylpropane sulfonic acid. The acidic groups can be present completely or partially as a sodium, potassium, ammonium, or mono- or triethanolammonium salt.

Preferred film-forming anionic polymers c) are acrylic acid/acrylamide copolymers and, in particular, polyacrylamide copolymers having sulfonic-acid-group-containing monomers. An especially preferred film-forming and setting anionic copolymer consists of 70 to 55 mol % of acrylamide and 30 to 45 mol % of 2-acrylamido-2-methylpropane sulfonic acid, wherein the sulfonic acid group can be present completely or partially as a sodium, potassium, ammonium, or mono- or triethanolammonium salt. This copolymer can also be cross-inked, wherein preferably polyolefinically unsaturated compounds such as tetraallyloxyethane, allyl sucrose, allyl pentaerythritol, and methylenebisacrylamide are used as cross-linking agents. Such a polymer is contained in the commercial product Sepigel® 305 from the company SEPPIC. The use of said commercial product, which contains a hydrocarbon mixture ($C_3$-$C_{14}$ isoparaffin) and a non-ionogenic emulsifier (Laureth-7) in addition to the polymer component, can be advantageous as contemplated herein.

The sodium acryloyldimethyltaurate copolymers sold under the name Simulgel® 600 as a compound with isohexadecane and polysorbate 80 can likewise be advantageous as contemplated herein.

Likewise preferred film-forming and setting anionic homopolymers c) are uncross-linked and cross-linked polyacrylic acids. Allyl ethers of pentaerythritol, of sucrose, and of propylene can be preferred cross-linking agents. Such compounds are commercially available, for example, under the trademark Carbopol®.

Other film-forming and setting anionic polymers c) that can be used with preference are selected from at least one polymer of the group consisting of
- copolymers of vinyl acetate and crotonic acid (which are marked, for example, in a 60 wt % dispersion in isopropanol-water by the company CIBA as the commercial product Aristoflex® A 60 with the INCI name VA/Crotonates Copolymer),
- copolymers of ethyl acrylate and methacrylic acid (which are sold, for example, in an approximately about 20 to about 30 wt % dispersion in water by BASF SE under the trade name Luviflex® Soft with an acid number of 84 to 105 and with the INCI name Acrylates Copolymer),
- polyurethanes having at least one carboxyl group (such as a copolymer of isophthalic acid, adipic acid, 1,6-hexanediol, neopentyl glycol, and isophorone diisocyanate, which is sold by the company BASF SE under the trade name Luviset PUR with the INCI name Polyurethane-1 or under the trade name Luviset Shape with the INCI name Polyurethane-34).

To further optimize the product properties, particularly to increase the product stability and to increase the hair care properties (texture, combability, elasticity, softness), it has proven advantageous if the cosmetic agents as contemplated herein also contain at least one surfactant, wherein the surfactant can, in principle, be of a non-ionic, anionic, cationic, and/or ampholytic nature.

The group of the ampholytic or amphoteric surfactants comprises zwitterionic surfactants and ampholytes. As contemplated herein, the surfactants can already have an emulsifying effect. In this embodiment of the disclosure, the use of at least one non-ionic surfactant or emulsifier and/or at least one cationic surfactant is especially preferred.

The one or more surfactants are contained in the cosmetic agents as contemplated herein preferably in an amount of about 0.01 to about 5.00 wt %, more preferably about 0.05 to about 4.00 wt %, and particularly about 0.10 to about 3.00 wt %, wherein the amount specifications relate to the total weight of the cosmetic agents.

It has proven especially preferred if the cosmetic agents as contemplated herein additionally contain at least one non-ionic surfactant and/or one non-ionic emulsifier.

Suitable nonionic surfactants and/or emulsifiers contain, for example, a polyol group, a polyalkylene glycol ether group, or a combination of polyol group and polyglycol ether group as a hydrophilic group. Such compounds are, for example,
- products of the addition of 2 to 100 mol of ethylene oxide and/or 1 to 5 mol of propylene oxide to linear and branched fatty alcohols having 8 to 30 carbon atoms, to fatty acids having 8 to 30 carbon atoms, and to alkylphenols having 8 to 15 carbon atoms in the alkyl group,
- products of the addition of 2 to 50 mol of ethylene oxide and/or 1 to 5 mol of propylene oxide to linear and branched fatty alcohols having 8 to 30 carbon atoms, to fatty acids having 8 to 30 carbon atoms, and to alkylphenols having 8 to 15 carbon atoms in the alkyl group, said products being end-capped with a methyl residue or C₂—C alkyl residue, such as the types available under the sales names Dehydol® LS and Dehydol® LT (Cognis),
C$_{12}$-C$_{30}$ fatty acid mono- and diesters of products of the addition of 1 to 30 mol of ethylene oxide to glycerol,
products of the addition of 5 to 60 mol of ethylene oxide to castor oil and hardened castor oil,
polyol fatty acid esters, such as the commercial product Hydagen® HSP (Cognis) or Sovermol types (Cognis),
alkoxylated triglycerides,
alkoxylated fatty acid alkyl esters of formula (T-I),

$$R^1CO-(OCH_2CHR^2)_wOR^3 \quad (T-I)$$

in which R¹CO represents a linear or branched, saturated and/or unsaturated acyl residue having 6 to 22 carbon atoms, R² represents hydrogen or methyl, R³ represents linear or branched alkyl residues having 1 to 4 carbon atoms, and w represents numbers from 1 to 20,
amine oxides,
hydroxy mixed ethers, which are described, for example, in laid-open application DE 19738866,
sorbitan fatty acid esters and products of the addition of ethylene oxide to sorbitan fatty acid esters, such as the polysorbates,
sugar fatty acid esters and products of the addition of ethylene oxide to sugar fatty acid esters,
products of the addition of ethylene oxide to fatty acid alkanolamides and fatty amines,
sugar surfactants of the type of the alkyl and alkenyl oligoglycosides according to formula (T-II),

$$R^4O-[G]_p \quad (T-II)$$

in which R⁴ represents an alkyl or alkenyl residue having 4 to 22 carbon atoms, G represents a sugar residue having 5 or 6 carbon atoms, and p represents numbers from 1 to 10.

The alkyl and alkenyl oligoglycosides can be derived from aldoses or ketoses having 5 or 6 carbon atoms, preferably from glucose. The preferred alkyl and/or alkenyl oligoglycosides are therefore alkyl and/or alkenyl oligoglucosides. The index number p in general formula (T-II) indicates the degree of oligomerization, i.e., the distribution of mono- and oligoglycosides, and represents a number between 1 and 10. While p must always be an integer in the individual molecule, and can assume especially the values p=1 to 6 here, the value p for a certain alkyl oligoglycoside is an analytically determined calculated value, which is usually a rational number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and in particular between 1.2 and 1.4 are preferred from the perspective of application.

The alkyl or alkenyl residue R⁴ can be derived from primary alcohols having 4 to 11, preferably 8 to 10 carbon atoms. The alkyl or alkenyl residue R⁴ can also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and technical mixtures thereof, which can be obtained as described above. Alkyl oligoglucosides based on hardened C$_{12/14}$ coconut alcohol having a degree of oligomerization of 1 to 3 are preferred.

The PEG derivatives of hydrogenated castor oil have been found to be exceedingly preferred non-ionic surfactants and/or emulsifiers. Said PEG derivatives of hydrogenated castor oil are generally commercially available under the name PEG Hydrogenated Castor Oil. Especially preferred as contemplated herein are, for example, PEG-30 Hydrogenated Castor Oil, PEG-33 Hydrogenated Castor Oil, PEG-35 Hydrogenated Castor Oil, PEG-36 Hydrogenated Castor Oil, PEG-40 Hydrogenated Castor Oil, and/or PEG-60 Hydrogenated Castor Oil. The use of PEG-40 Hydrogenated Castor Oil as a non-ionic emulsifier is especially preferred as contemplated herein.

Another preferred embodiment of the disclosure is characterized in that the cosmetic agent additionally contains about 0.05 to about 1.50 wt %, especially preferably about 0.10 to about 1.00 wt %, and particularly about 0.15 to about 0.70 wt % of at least one non-ionic emulsifier, preferably one PEG derivative of hydrogenated castor oil, wherein the amount specifications relate to the total weight of the cosmetic agent.

The use of PEG-40 Hydrogenated Castor Oil in the agents as contemplated herein in the amounts stated above is particularly preferred.

Furthermore, it has proven especially preferred if the cosmetic agents as contemplated herein additionally contain at least one cationic surfactant to increase the hair care properties.

Cationic surfactants of the type of the quaternary ammonium compounds, the esterquats, and the amidoamines can be used as contemplated herein. Preferred quaternary ammonium compounds are ammonium halides, particularly chlorides and bromides, such as alkyltrimethylammonium chlorides, dialkyldimethylammonium chlorides, and trialkylmethylammonium chlorides. The long alkyl chains of these surfactants preferably have 10 to 18 carbon atoms, such as in cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride. Other preferred cationic surfactants are the imidazolium compounds known under the INCI names Quaternium-27 and Quaternium-83.

Especially preferably alkyltrimethylammonium salts, exceedingly preferably C$_{12}$-C$_{20}$-alkyltrimethylammonium salts, and particularly C$_{16}$-C$_{18}$-alkyltrimethylammonium chlorides can be used.

Another preferred embodiment of the disclosure is characterized in that the cosmetic agent additionally contains about 0.05 to about 5.00 wt %, especially preferably about 0.10 to about 4.00 wt %, and particularly about 020 to about 3.00 wt % of at least one surfactant, preferably at least one cationic surfactant, wherein the amount specifications relate to the total weight of the cosmetic agent.

Especially preferred is the use of C$_{12}$-C$_{20}$-alkyltrimethylammonium salts and, in particular, of C$_{16}$-C$_{18}$-alkyltrimethylammonium chlorides in the agents as contemplated herein in the amounts stated above.

In principle, all anionic surface-active substances suitable for use on the human body are suitable as anionic surfactants. These are characterized by a water-solubilizing anionic group, such as a carboxylate, sulfate, sulfonate, or phosphate group, and a lipophilic alkyl group having approximately 8 to 30 carbon atoms. In addition, glycol or polyglycol ether groups, ester, ether, and amide groups, and hydroxyl groups can be contained in the molecule. Examples of suitable anionic surfactants are, in each case in the form of the sodium, potassium, and ammonium salts and the mono-, di-, and trialkanolammonium salts having 2 to 4 carbon atoms in the alkanol group, linear and branched fatty acids having 8 to 30 carbon atoms (soaps), ether carboxylic acids of the formula R—O—(CH$_2$—CH$_2$O)$_x$—CH$_2$—COOH, in which R is a linear alkyl group having 8 to 30 carbon atoms and x=0 or 1 to 16, acyl sarcosides having 8 to 24 carbon atoms in the acyl group, acyl taurides having 8 to 24 carbon atoms in the acyl group, acyl isethionates having 8 to 24 carbon atoms in the acyl group, sulfosuccinic acid mono- and dialkyl esters having 8 to 24 carbon atoms in the alkyl group and sulfosuccinic acid monoalkyl polyoxyethyl esters having 8 to 24 carbon atoms in the alkyl group and 1 to 6 oxyethyl groups, linear alkane sulfonates having 8 to 24 carbon atoms, linear alpha-olefin sulfonates having 8 to 24 carbon atoms, alpha-sulfo fatty acid methyl esters of fatty acids having 8 to 30 carbon atoms, alkyl sulfates and alkyl polyglycol ether sulfates of the formula R—O(CH$_2$—CH$_2$O)$_x$—OSO$_3$H, in which R is a preferably linear alkyl group having 8 to 30 carbon atoms and x=0 or 1 to 12, mixtures of surface-active hydroxysulfonates, sulfated hydroxyalkyl polyethylene and/or hydroxyalkylene propylene glycol ethers, sulfonates of unsaturated fatty adds having 8 to 24 carbon atoms and 1 to 6 double bonds, esters of tartaric acid and citric acid with alcohols that are products of the addition of approximately 2 to 15 molecules of ethylene oxide and/or propylene oxide to fatty alcohols having 8 to 22 carbon atoms, alkyl and/or alkenyl ether phosphates of formula (T-V),

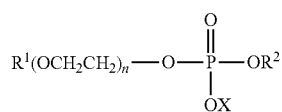

(T-V)

in which R$^1$ preferably represents an aliphatic hydrocarbon residue having 8 to 30 carbon atoms, R$^2$ represents hydrogen, a residue (CH$_2$CH$_2$O)$_n$R$^1$, or X, n represents numbers from 1 to 10, and X represents hydrogen, an alkali metal or alkaline-earth metal, or NR$^3$R$^4$R$^5$R$^6$, with R$^3$ to R$^6$ representing, independently of each other, hydrogen or a C$_1$ to C$_4$ hydrocarbon residue, sulfated fatty acid alkylene glycol esters of formula (T-VI), R$^7$CO(AlkO)$_n$SO$_3$M     (T-VI)

in which R$^7$CO— represents a linear or branched, aliphatic, saturated and/or unsaturated acyl residue having 6 to 22 carbon atoms, Alk represents CH$_2$CH$_2$, CHCH$_3$CH$_2$, and/or CH$_2$CHCH$_3$, n represents numbers from 0.5 to 5, and M represents a cation, monoglyceride sulfates and monoglyceride ether sulfates of formula (T-VII),

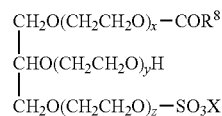

(T-VII)

in which R$^8$CO represents a linear or branched acyl residue having 6 to 22 carbon atoms, x, y, and z represent, in total, 0 or numbers from 1 to 30, preferably 2 to 10, and X represents an alkali metal or alkaline-earth metal. Typical examples of monoglyceride (ether) sulfates suitable as contemplated herein are the products of the reaction of lauric acid monoglyceride, coconut fatty acid monoglyceride, palmitic acid monoglyceride, stearic acid monoglyceride, oleic acid monoglyceride, and tallow fatty acid monoglyceride and ethylene oxide adducts thereof with sulfur trioxide or chlorosulfuric acid in the form of the sodium salts thereof. Monoglyceride sulfates of formula (T-VII), in which R$^8$CO represents a linear acyl residue having 8 to 18 carbon atoms, are preferably used, amide ether carboxylic acids, condensation products of C$_8$-C$_{30}$ fatty alcohols with protein hydrolysates and/or amino acids and derivatives thereof, which are known to a person skilled in the art as protein fatty acid condensates, such as the Lamepon® types, the Gluadin® types, Hostapon® KCG, or the Amisoft® types.

Surface-active compounds that bear at least one quaternary ammonium group and at least one —COO$^{(-)}$ or —SO$_3$$^{(-)}$ group in the molecule are referred to as zwitterionic surfactants. Especially suitable zwitterionic surfactants are the betaines such as the N-alkyl-N,N-dimethylammonium glycinates, for example coco alkyl dimethyl ammonium glycinate, N-acyl-aminopropyl-N,N-dimethylammonium glycinates, for example cocoacyl aminopropyl dimethyl ammonium glycinate, and 2-alkyl-3-carboxymethyl-3-hydroxyethyl-imidazolines each having 8 to 18 C atoms in the alkyl or acyl group, and cocoacyl aminoethyl hydroxyethyl carboxymethyl glycinate. A preferred zwitterionic surfactant is the fatty acid amide derivative known under the INCI name Cocamidopropyl Betaine.

The term "ampholytes" is understood to mean surface-active compounds that contain at least one free amino group and at least one —COOH or —SO$_3$H group in addition to a C$_8$-C$_{24}$ alkyl or acyl group in the molecule and are capable of forming inner salts. Examples of suitable ampholytes are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids each having approximately 8 to 24 carbon atoms in the alkyl group. Especially preferred ampholytes are N-cocoalkylaminopropionate, cocoacylaminoethylaminopropionate, and C$_{12}$-C$_{18}$ acyl sarcosine.

According to another preferred embodiment, the cosmetic agents as contemplated herein exist as a foam. For this purpose, the agents as contemplated herein are packaged in a dispensing device, which is either a compressed-gas container (aerosol container) additionally filled with a propellant or a non-aerosol container. By definition, the compressed-gas containers used to distribute a product via a valve by means of the internal gas pressure of the container are called "aerosol containers". Conversely to the aerosol definition, a container under normal pressure used to distribute a product by means of mechanical action by a pumping or squeezing system is defined as a "non-aerosol container".

In this embodiment, the cosmetic agents as contemplated herein particularly preferably exist as an aerosol foam in an aerosol container. The agent as contemplated herein therefore preferably additionally contains at least one propellant.

Agents as contemplated herein in the form of an aerosol product can be produced in a typical manner. In general, all constituents of the agent as contemplated herein with the exception of the propellant are introduced into a suitable pressure-resistant container. The container is then closed with a valve. Finally, the desired amount of propellant is introduced by conventional techniques.

In the embodiment as an aerosol foam, propellants suitable as contemplated herein are selected, for example, from $N_2O$, dimethyl ether, $CO_2$, air, alkanes having 3 to 5 carbon atoms, such as propane, n-butane, isobutane, n-pentane, and isopentane, and mixtures thereof.

According to the embodiment of an aerosol foam, the mentioned alkanes, mixtures of the mentioned alkanes, or mixtures of the mentioned alkanes with dimethyl ether are used as a single propellant. However, the disclosure expressly also comprises the additional use of propellants of the type of the hydrochlorofluorocarbons, particularly the hydrofluorocarbons. Dimethyl ether, propane, n-butane, isobutane, and mixtures thereof are preferred. Mixtures of propane and butane are extremely preferably used as a sole propellant in a weight ratio of propane to butane of 70:30 to 15:85. Said mixtures are, in turn, preferably used in the cosmetic agents as contemplated herein in an amount of 1 to 15 wt %, with respect to the weight of the entire agent. As contemplated herein, the term "butane" is understood to mean n-butane, isobutane, and mixtures of n-butane and isobutane.

Another preferred embodiment of the disclosure is characterized in that the cosmetic agent contains preferably about 1 to about 15 wt %, especially preferably about 2 to about 12.5 wt %, and particularly about 3 to about 10 wt % of at least one propellant, preferably propane and/or butane, with respect to the total weight of the cosmetic agent.

The cosmetic agents as contemplated herein can contain further auxiliary substances, care substances, and additives. The proportion by weight of the further ingredients contained in the agents as contemplated herein in addition to the components a) to c), particularly the further auxiliary substances, care substances, and additives contained in these compositions, is preferably less than 10 wt %, more preferably less than 7.0 wt %, especially preferably less than 5.0 wt %, and particularly less than 3.0 wt %, with respect to the total weight of the agents as contemplated herein. The proportion by weight of said auxiliary substances, care substances, and additives can be, for example, about 0.1 to about 5.0 wt %, particularly about 0.2 to about 3.0 wt %, with respect to the total weight of the cosmetic agents as contemplated herein.

The cosmetic composition can contain, for example, a protein hydrolysate and/or one of the derivatives thereof as a care substance. Protein hydrolysates are product mixtures that are obtained by the acidically, basically, or enzymatically catalyzed decomposition of proteins. As contemplated herein, the term "protein hydrolysates" is understood to also mean total hydrolysates, individual amino acids and derivatives thereof, and mixtures of different amino acids. The molecular weight of the protein hydrolysates that can be used as contemplated herein is between about 75 daltons, the molar weight of glycine, and about 200,000 daltons. The molar weight is preferably about 75 to about 50,000 daltons and exceedingly preferably about 75 to about 20,000 daltons.

Cationic polymers that have both care properties and film-forming and/or setting properties are considered as another care substance. Especially suitable for use in the agents as contemplated herein are, for example:

N-vinylpyrrolidone/1-vinyl-3-methyl-1H-imidazolium chloride copolymers (such as polymers having the INCI name Polyquaternium-16 under the trade names Luviquat® Style, Luviquat® FC 370, Luviquat® FC 550, Luviquat® FC 905, and Luviquat® HM 552 (BASF SE)), N-vinylpyrrolidone/1-vinyl-3-methyl-1H-imidazolium methyl sulfate copolymers (such as polymers having the INCI name Polyquaternium-44 under the trade name Luviquat® Care (BASF SE)), N-vinylpyrrolidone/N-vinylcaprolactam/1-vinyl-3-methyl-1H-imidazolium terpolymers (such as polymers having the INCI name Polyquaternium-46 under the trade names Luviquat® Care or Luviquat® Hold (BASF SE)), N-vinylpyrrolidone/methacrylamide/N-vinylimidazole/1-vinyl-3-methyl-1H-imidazolium methyl sulfate copolymers (such as the polymers having the INCI name Polyquaternium-68 under the trade name Luviquat® Supreme (BASF SE)), and mixtures of these polymers.

Furthermore, the cosmetic agents as contemplated herein can contain at least one vitamin, one provitamin, one vitamin precursor, and/or one of the derivatives thereof as a care substance. As contemplated herein, vitamins, provitamins, and vitamin precursors that are typically assigned to the groups A, B, C, E, F, and H are preferred.

Especially preferred are the vitamins of the groups A, B, and E, particularly niacinamide, panthenol, and/or biotin.

Furthermore, the cosmetic agents as contemplated herein can contain at least one plant extract, or mono- or oligosaccharides and/or lipids, as a care substance.

The cosmetic agents as contemplated herein can also contain UV filters as care substances, which UV filters can typically be used in amounts of about 0.01 to about 1 wt %, with respect to the total weight of the agents as contemplated herein.

A second subject matter of the disclosure is the use of a cosmetic agent of the first subject matter of the disclosure to increase the volume and the body of hair and to improve the curl retention, particularly the high-humidity curl retention.

Examples

1) The composition of some preferred cosmetic compositions can be found in the following table (specifications in wt % with respect to the total weight of the composition, unless otherwise indicated)

|  | Formula 1 | Formula 2 | Formula 3 | Formula 4 |
| --- | --- | --- | --- | --- |
| Chitosan or chitosan derivative | 0.05-1.50 | 0.10-1.40 | 0.15-1.25 | 0.20-1.00 |
| Hydrophobic pyrogenic silicic acid | 0.05-1.50 | 0.10-1.40 | 0.15-1.25 | 0.20-1.00 |

-continued

|  |  |  |  |  |
|---|---|---|---|---|
| Non-ionic, anionic, or amphoteric film-forming polymer | 0.10-7.00 | 0.20-5.00 | 0.25-4.00 | 0.30-3.00 |
| Water and other ingredients | Ad 100 | Ad 100 | Ad 100 | Ad 100 |
|  | Formula 5 | Formula 6 | Formula 7 | Formula 8 |
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Hydrophobic pyrogenic silicic acid | 0.05-1.50 | 0.10-1.40 | 0.15-1.25 | 0.20-1.00 |
| Non-ionic, anionic, or amphoteric film-forming polymer | 0.10-7.00 | 0.20-5.00 | 0.25-4.00 | 0.30-3.00 |
| Water and other ingredients | Ad 100 | Ad 100 | Ad 100 | Ad 100 |
|  | Formula 9 | Formula 10 | Formula 11 | Formula 12 |
| Chitosan or chitosan derivative | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Non-ionic, anionic, or amphoteric film-forming polymer | 0.10-7.00 | 0.20-5.00 | 0.25-4.00 | 0.30-3.00 |
| Water and other ingredients | Ad 100 | Ad 100 | Ad 100 | Ad 100 |
|  | Formula 13 | Formula 14 | Formula 15 | Formula 16 |
| Chitosan or chitosan derivative | 0.05-1.50 | 0.10-1.40 | 0.15-1.25 | 0.20-1.00 |
| Hydrophobic pyrogenic silicic acid | 0.05-1.50 | 0.10-1.40 | 0.15-1.25 | 0.20-1.00 |
| Non-ionic film-forming polymer | 0.10-7.00 | 0.20-5.00 | 0.25-4.00 | 0.30-3.00 |
| Water and other ingredients | Ad 100 | Ad 100 | Ad 100 | Ad 100 |
|  | Formula 17 | Formula 18 | Formula 19 | Formula 20 |
| Chitosan or chitosan derivative | 0.05-1.50 | 0.10-1.40 | 0.15-1.25 | 0.20-1.00 |
| Hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Water and other ingredients | Ad 100 | Ad 100 | Ad 100 | Ad 100 |
|  | Formula 21 | Formula 22 | Formula 23 | Formula 24 |
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Water and other ingredients | Ad 100 | Ad 100 | Ad 100 | Ad 100 |
|  | Formula 25 | Formula 26 | Formula 27 | Formula 28 |
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Surfactant | 0.05-5.00 | 0.10-4.00 | 0.15-3.50 | 0.20-3.00 |
| Water and other ingredients | Ad 100 | Ad 100 | Ad 100 | Ad 100 |
|  | Formula 29 | Formula 30 | Formula 31 | Formula 32 |
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |

-continued

|  | | | | |
|---|---|---|---|---|
| Cationic surfactant | 0.05-5.00 | 0.10-4.00 | 0.15-3.50 | 0.20-3.00 |
| Water and other ingredients | Ad 100 | Ad 100 | Ad 100 | Ad 100 |

|  | Formula 33 | Formula 34 | Formula 35 | Formula 36 |
|---|---|---|---|---|
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Non-ionic emulsifier, preferably PEG-40 Hydrogenated Castor Oil | 0.05-1.50 | 0.10-1.20 | 0.10-1.00 | 0.15-0.70 |
| Water and other ingredients | Ad 100 | Ad 100 | Ad 100 | Ad 100 |

|  | Formula 37 | Formula 38 | Formula 39 | Formula 40 |
|---|---|---|---|---|
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Cationic surfactant | 0.05-5.00 | 0.10-4.00 | 0.15-3.50 | 0.20-3.00 |
| Non-ionic emulsifier, preferably PEG-40 Hydrogenated Castor Oil | 0.05-1.50 | 0.10-1.20 | 0.10-1.00 | 0.15-0.70 |
| Water and other ingredients | Ad 100 | Ad 100 | Ad 100 | Ad 100 |

|  | Formula 41 | Formula 42 | Formula 43 | Formula 44 |
|---|---|---|---|---|
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Surfactant | 0.05-5.00 | 0.10-4.00 | 0.15-3.50 | 0.20-3.00 |
| Propellant, particularly propane/butane | 1.00-15.00 | 2.00-12.50 | 3.00-10.00 | 3.50-9.00 |
| Water and other ingredients | Ad 100 | Ad 100 | Ad 100 | Ad 100 |

|  | Formula 45 | Formula 46 | Formula 47 | Formula 48 |
|---|---|---|---|---|
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Cationic surfactant | 0.05-5.00 | 0.10-4.00 | 0.15-3.50 | 0.20-3.00 |
| Propellant, particularly propane/butane | 1.00-15.00 | 2.00-12.50 | 3.00-10.00 | 3.50-9.00 |
| Water and other ingredients | Ad 100 | Ad 100 | Ad 100 | Ad 100 |

|  | Formula 49 | Formula 50 | Formula 51 | Formula 52 |
|---|---|---|---|---|
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Non-ionic emulsifier, preferably PEG-40 Hydrogenated Castor Oil | 0.05-1.50 | 0.10-1.20 | 0.10-1.00 | 0.15-0.70 |

-continued

|  | | | | |
|---|---|---|---|---|
| Propellant, particularly propane/butane | 1.00-15.00 | 2.00-12.50 | 3.00-10.00 | 3.50-9.00 |
| Water and other ingredients | Ad 100 | Ad 100 | Ad 100 | Ad 100 |

|  | Formula 53 | Formula 54 | Formula 55 | Formula 56 |
|---|---|---|---|---|
| Neutralization product of chitosan with hydrochloric acid, lactic acid, formic acid, pyrrolidone carboxylic acid, nicotinic acid, and/or hydroxybutyric acid | 0.05-1.50 | 0.10-1.40 | 0.15-1.25 | 0.20-1.00 |
| Alkyl-group-modified hydrophobic pyrogenic silicic acid | 0.05-1.50 | 0.10-1.40 | 0.15-1.25 | 0.20-1.00 |
| Polyvinylpyrrolidone and/or vinyl acetate/vinylpyrrolidone copolymer | 0.10-7.00 | 0.20-5.00 | 0.25-4.00 | 0.30-3.00 |
| Cationic surfactant | 0.05-5.00 | 0.10-4.00 | 0.15-3.50 | 0.20-3.00 |
| Non-ionic emulsifier, preferably PEG-40 Hydrogenated Castor Oil | 0.05-1.50 | 0.10-1.20 | 0.10-1.00 | 0.15-0.70 |
| Propellant, particularly propane/butane | 1.00-15.00 | 2.00-12.50 | 3.00-10.00 | 3.50-9.00 |
| Water and other ingredients | Ad 100 | Ad 100 | Ad 100 | Ad 100 |

|  | Formula 57 | Formula 58 | Formula 59 | Formula 60 |
|---|---|---|---|---|
| Hydamer ®[1] HCMF | 0.05-1.50 | 0.05-1.50 | 0.05-1.50 | 0.05-1.50 |
| Aerosil ®[2] R 972 | 0.05-1.50 | 0.05-1.50 | 0.05-1.50 | 0.05-1.50 |
| Luviskol ®[3] K 90 | 0.10-7.00 | 0.10-7.00 | 0.10-7.00 | 0.10-7.00 |
| PVP/VA Copolymer 60/40, 50% AS | 1.00-5.00 |  |  | 1.00-5.00 |
| Luviquat ®[4] FC 370 |  | 0.50-5.00 |  | 0.50-5.00 |
| Dehyguare ®[5] A CA |  |  | 0.50-2.00 | 0.50-2.00 |
| PEG-40 Hydrogenated Castor Oil | 0.05-1.50 | 0.05-1.50 | 0.05-1.50 | 0.05-1.50 |
| Propane/butane | 1.00-10.00 | 1.00-10.00 | 1.00-10.00 | 1.00-10.00 |
| Acidulant, preservative agent, perfume | 0.50-2.00 | 0.50-2.00 | 0.50-2.00 | 0.50-2.00 |
| Water | Ad 100 | Ad 100 | Ad 100 | Ad 100 |

List of the raw materials used:
1 INCI name: Chitosan; Chitinor AS
2 INCI name: Silica Dimethyl Silylate; Evonik
3 INCI name: PVP; 20% AS; BASF
4 INCI name: Polyquaternium-16, approx. 35% AS; BASF
5 INCI name: Aqua, Cetrimonium Chloride, approx. 25% AS; BASF 2) Verifications of action The following compositions as contemplated herein (6) and not as contemplated herein (1-5) were produced and examined in the laboratory with regard to curl retention and volume/body (ring method) (the amount specifications in the table relate to wt %):

|  | 1 | 2 | 3 | 4 | 5 | 6 |
|---|---|---|---|---|---|---|
| a): Hydamer ® HCMF | 0.3 |  | 0.2 |  | 0.5 | 0.5 |
| c): Luviskol ® K 85 | 6.0 |  |  |  | 1.5 |  |
| c): Luviskol ® K 90 (20% AS) |  |  |  |  |  | 1.5 |
| c): PVP/VA Copolymer 60/40 (50% AS) |  | 13 | 4.0 | 6.5 | 4.0 | 4.0 |
| b) Aerosil ® R972 |  |  |  | 0.5 |  | 0.5 |
| Dehyquart ® A CA | 1.0 |  | 1.0 | 0.9 | 1.0 | 1.0 |
| Behentrimonium chloride |  | 0.4 |  |  |  |  |
| PEG-40 Hydrogenated Castor Oil | 0.2 |  | 0.2 |  | 0.2 | 0.2 |
| Propane-butane | 6.0 |  | 6.0 | 10 | 6.0 | 6.0 |
| n-Butane |  | 5.0 |  |  |  |  |
| Dimethyl ether |  | 10 |  |  |  |  |
| Preservative agent, acidulant, perfume, water | Ad 100 | Ad 100 | Ad 100 | Ad 100 | Ad 100 | Ad 100 | a) Test of Curl Retention

Each of the compositions mentioned above was tested on 10 hair strands, which were approximately 1 g in weight and 20 cm in length. The strands were twice washed with a 14% sodium laureth sulfate solution and rinsed with water. Thereafter, 3.5 cm³ of the compositions 1-6 were applied to each strand, and the strands were then wound around spiral curlers (6 mm diameter and 160 mm length).

The strands were dried in a drying cabinet at $(45\pm1)°$ C. for one hour and then allowed to rest for 18 hours at $(22\pm1)°$ C. and $(65\pm5)\%$ humidity.

Thereafter, the strands were carefully removed from the curlers and placed in a climatic chamber $((21\pm1)°$ C. and $(85\pm5)\%$ humidity), each strand being fastened at the upper end of the strand. The length of each strand was measured before being fastened in the climatic chamber (L0) and after 13, 30, 60, and 90 minutes and 2, 3, 4, 5, and 8 hours in the climatic chamber. The curl retention was determined in % in accordance with the following equation:

$$\text{Curl Retention } [\%] = \frac{L - Lt}{L - L0} * 100,$$

wherein

L means the length of the strands before being wound onto the curlers,

L0 means the length of the strands before being placed in the climatic chamber, and Lt means the length of the strands after each period of time in the climatic chamber.

The values that were determined after 8 hours are compiled in the following table (average value of 10 measured hair strands). It is clear that the hair strands that were treated with the compositions as contemplated herein exhibit the best curl retention ability.

| Measurement | Curl retention (average values) [%] | | | | | |
|---|---|---|---|---|---|---|
| | 1 | 2 | 3 | 4 | 5 | 6 |
| 8 hours | 45.7 | 38.4 | 44.8 | 40.9 | 44.8 | 49.1 | b) Test of Volume and Body in Accordance with the Ring Method

The volume and body of the hair are determined by pulling a hair strand through a metal ring of a specific diameter and, at the same time, measuring the force required for this. The more resistant the strands are to the deformation (body), the more force must be applied.

Each of the compositions 1-6 was tested on 10 hair strands (weight of 3 g and length of 20 cm). Before the test was performed, the hair strands were washed twice with a 14% sodium laureth sulfate solution, dried (for one hour in a drying cabinet at (45±1)° C.), and then allowed to rest for 18 hours at (22±1)° C. and (50±5)% humidity.

Then the compositions 1-6 (3.5 cm$^3$ per 1 g of hair) were applied to the 50% moist strands and massaged in for 1 minute. To generate volume, the strands were wound onto rollers, dried for 45 minutes at 45° C., and allowed to rest overnight at 20° C. and 65% humidity.

After being removed from the rollers, the strands were combed with a metal comb with the same number of comb strokes in each case.

The strands treated in such a way were then pulled through rings of decreasing diameter (20 mm and 12 mm), and the force required for this was measured.

The following table shows the test results of the measurements for "tactile volume/body" for the ring diameter of 12 mm (average value of 10 measured hair strands). It is clear that the hair strands that were treated with the compositions as contemplated herein exhibited the best values for "body".

| | 1 | 2 | 3 | 4 | 5 | 6 | Untr. |
|---|---|---|---|---|---|---|---|
| Body (resistance) | 7.9 | 6.7 | 7.2 | 8.7 | 8.3 | 14.5 | 6.6 |
| Standard deviation | 0.7 | 0.5 | 0.6 | 0.6 | 0.8 | 1.4 | 0.7 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A cosmetic agent for temporarily shaping keratin-containing fibers, comprising:
    a cosmetic carrier;
    at least one chitosan or derivative thereof in an amount of from about 0.2 to about 1 wt. % based on the total weight of the cosmetic agent, the at least one chitosan or derivative thereof comprising an at least partially deacetylated chitosan;
    at least one hydrophobic pyrogenic silicic acid in an amount of from about 0.2 to 1 wt. % based on the total weight of the cosmetic agent, the at least one hydrophobic pyrogenic silicic acid modified at the surface with hydrophobic groups comprising alkyl groups; and
    at least one non-ionic film-forming polymer in an amount of from about 2 to about 7 wt. % based on the total weight of the cosmetic agent, the at least one non-ionic film-forming polymer comprising at least one homopolymer or copolymer of vinylpyrrolidone.

2. The cosmetic agent according to claim 1, wherein at least one neutralization product of chitosan with at least one acid is contained as a chitosan or derivative thereof.

3. The cosmetic agent according to claim 2, wherein the acid is selected from inorganic acids, organic carboxylic acids, or mixtures of these acids.

4. The cosmetic agent according to claim 1, wherein the at least one hydrophobic pyrogenic silicic acid comprises a compound known under the INCI name Silica Dimethyl Silylate.

5. The cosmetic agent according to claim 1, wherein the cosmetic agent additionally comprises at least one surfactant.

6. The cosmetic agent according to claim 1, wherein the cosmetic agent additionally comprises at least one non-ionic emulsifier.

7. The cosmetic agent according to claim 1, wherein the cosmetic agent comprises water and/or a water-alcohol mixture.

8. The cosmetic agent according to claim 1, wherein the cosmetic agent comprises at least one propellant.

9. The cosmetic agent according to claim 3, wherein the inorganic acid comprises hydrochloric acid.

10. The cosmetic agent according to claim 3, wherein the organic carboxylic acid comprises lactic acid, formic acid, pyrrolidone carboxylic acid, nicotinic acid, hydroxyisobutyric acid, hydroxyisovaleric acid, or mixtures of these acids.

11. The cosmetic agent according to claim 6, wherein the at least one non-ionic emulsifier comprises at least one PEG derivative of hydrogenated castor oil.

12. The cosmetic agent according to claim 8, wherein the at least one propellant comprises propane and/or butane.

13. A method for temporarily shaping keratin-containing fibers, the method comprising the step of using a cosmetic agent according to claim 1.

* * * * *